United States Patent [19]

Jacobs

[11] Patent Number: 5,472,589
[45] Date of Patent: Dec. 5, 1995

[54] RUGGEDIZED HIGH-VOLUME ENVIROMENTALLY-FRIENDLY ELECTROPHORETIC CELL

[76] Inventor: Michael Jacobs, 281 E. Avenue, Norwalk, Conn. 06855

[21] Appl. No.: 119,034

[22] Filed: Sep. 9, 1993

[51] Int. Cl.$^6$ .......................... G01N 27/26; G01N 27/447
[52] U.S. Cl. ....................... 204/299 R; 204/182.8
[58] Field of Search .............................. 204/299 R, 182.8

[56] References Cited

U.S. PATENT DOCUMENTS

| | | | |
|---|---|---|---|
| 4,035,377 | 7/1977 | Detroy | 204/299 R |
| 5,073,246 | 12/1991 | Chu et al. | 204/182.8 X |
| 5,284,565 | 2/1994 | Chu et al. | 204/299 R |

*Primary Examiner*—John Niebling
*Assistant Examiner*—John S. Starsiak, Jr.
*Attorney, Agent, or Firm*—Handal & Morofsky

[57] ABSTRACT

An electrophoretic cell comprising a base member defining a planar support surface is disclosed. A layer of electrophoretic gel medium is disposed on the planar plastic support surface. A glass top face is disposed over the layer of gel. The gel lies between the top face and the base member. Either the top face or the base member is made of transparent material. A plurality of reservoirs are defined between the top face and the base member by the top face and base member. The reservoirs are defined by a plurality of walls disposed between the top face and the base member, and may be integral with the base member. Two opposite edges of the electrophoretic cell are provided with a band of material which is adhered thereto whereby additional strength is provided to the electrophoretic cell.

13 Claims, 4 Drawing Sheets

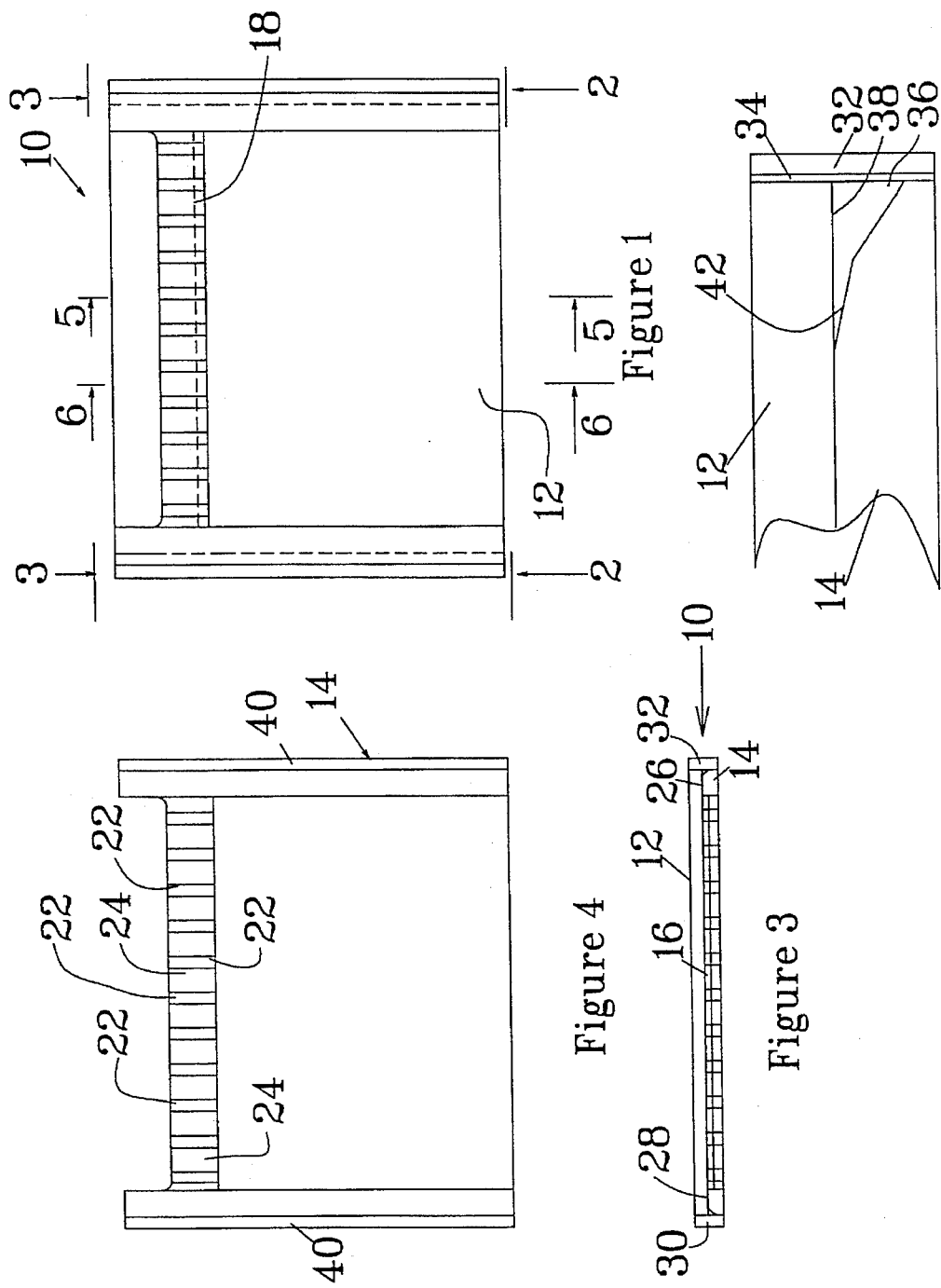

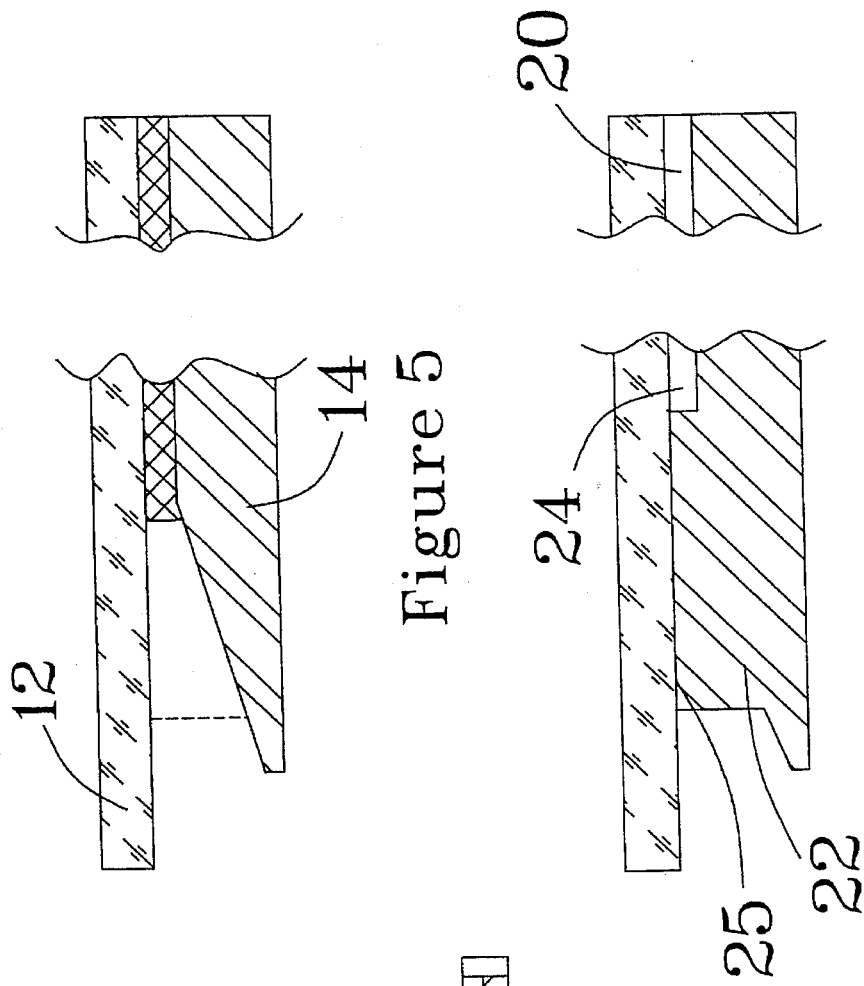
Figure 5
Figure 6
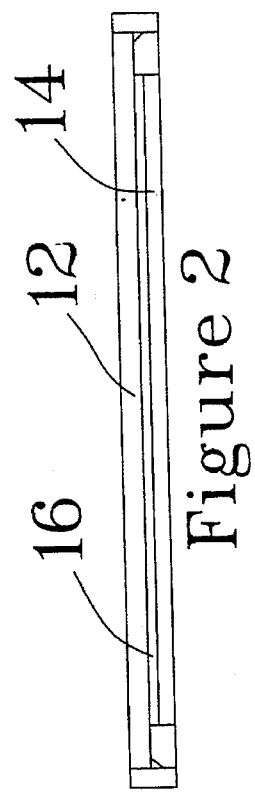
Figure 2

RUGGEDIZED HIGH-VOLUME ENVIROMENTALLY-FRIENDLY ELECTROPHORETIC CELL

TECHNICAL FIELD

The present invention relates to a novel construction of an electrophoretic cell for parallel multiple sample electrophoresis.

BACKGROUND

While the observation of electrophoretic phenomena was made at least as early as 1807 by the Russian physicist F. F. Reuss, it was not until the late 1930's that scientific applications of this technique came to see employment. This was largely on account of the work of Arne Tiselius.

Recognizing that in the migration of a particle through an electrophoretic material under the influence of an electric field, velocity is a function not only of field strength, but also certain of the particle's other characteristics, Tiselius built a cell using what is now referred to as the moving boundary method and provided it with a solution of plasma, postulating that plasma was not a homogeneous material. The experiment revealed that human plasma does indeed consist of a heterogeneous solution of materials, and identified for the first time alpha, beta and gamma globulins, each of which have different electrophoretic mobilities. As a consequence of this work, electrophoresis has been extensively used for many years whenever it is desired to separate solutions of proteins and other macromolecules.

Notwithstanding such widespread and longstanding use, the technique and apparatus of electrophoresis remains today much the same as it was in the time of Tiselius. Perhaps the only major change in the technology has been the introduction of gel as an electrophoretic medium.

Today, gel matrix electrophoresis is by far the most common form of electrophoresis. Gel matrices exhibit superior characteristics on account of their ability to substantially reduce to zero convective phenomena, which otherwise would distort the path of particles in the medium. Such convective phenomena introduce extremely large errors into the process in the case of conventional media. In addition, the use of gel supporting media also greatly reduces mixing of the various parts of the sample, and therefore provides for more stable separation.

Generally, electrophoretic mobility is a function of molecular size, molecular charge and molecular shape. It has been suggested that the molecular structure of the gel also provides a molecular sieving effect, resulting in greater resolving power where the molecules undergoing electrophoretic separation have different sizes. In addition, gels allow for the practical employment of gradients of pH and of reagents. Typically, such gradients are used in two dimensional arrays to provide a greater range of resolution.

For example, a widely employed use of a gel supporting media takes advantage of the incorporation into the gel matrix of a large amount of detergent which has the effect of denaturing or unbundling relatively tightly clustered protein molecule structures, to transform them into long flexible polymeric chains to which detergent molecules are bound. In this case, if the chains of the polymeric chains are of various lengths, even if they have uniform molecular characteristics, they will be caused to move through the electric field in the gel medium with a velocity which is determined by the length of the particular polymer. Since molecular weight is a function of polymer length, this method is used in a wide variety of applications where molecular weight is to be determined.

Typically, electrophoresis is carried out today in modular cells which comprise a layer of gel material, sandwiched between a pair of flat plastic or glass plates. Such cells contemplate the simultaneous and parallel running of a plurality of electrophoretic separation operations, each of which is carried out in its own elongated portion of the gel.

Typically a sample consisting of a weighted buffer solution and a known mixture of materials is used as a standard for the plurality of electrophoretic separations to be carried out simultaneously and in parallel with the separation of the known marker, all within the same cell and under the influence of the same electric field. Thus, a plurality of wells are cast into one end of the layer of gel and a known sample or marker, for example, of buffer and proteins is inserted into the first well. Unknown solutions of materials in buffer are then inserted into the other wells and an electric field applied across the cell. The result is migration of materials along parallel paths extending from the wells which are disposed side by side in the gel layer. After electrophoretic separation has been preformed, a dye is used to stain the separated materials, resulting in the revelation, typically, of a series of dark bands along each of the paths of electrophoretic separation.

By comparison of an unknown material to one or more electrophoretic separations contained within, typically, the same cell and of known characteristics, the characteristics of the unknown band may be determined by comparison to the marker. One typical application of such an operation is in the forensic field. For example, if a sample protein taken at the scene of a crime is known to consist of materials which may be electrophoretically separated, samples of similar proteins may be taken from suspects and the existence or nonexistence of a match used to determine the unique identity of the person from which the unknown sample originated because of the uniqueness of proteins in biosystems.

In accordance with the preferred embodiment, in order to provide parallel separation of input material for electrophoresis, it is necessary that the gel be formed with a plurality of input wells. In accordance with current practice, this is achieved by forming the gel with the desired wells. However, a problem is presented because of the fragile nature of the gel material. In particular, the wells cast into the material are likely to break and loose their integrity during handling, transport, packaging or the like. Thus, the common means employed by the industry to maintain structural integrity is to cast the wells using a comb. However, this comb is a relatively expensive item and thus raises the per unit cost of the electrophoretic cell. In addition, the use of the comb also complicates assembly requiring additional effort and expense during the same.

The use of the comb, which is generally cut from a planar sheet of material, presents an interesting problem for optimization in the design of the electrophoretic cell. In particular, a comb must have the same thickness as the gel medium in which electrophoresis is being carried out. If this were not the case, the possibility would exist for the migration of sample into the sides of the well if, for example, the comb were thinner than the gel. This would result in the substantial waste of extremely large amounts of what may be a very precious sample. Indeed, such a possibility cannot be tolerated. Rather, the interface between the sample in the solution and the electrophoretic gel medium must be strictly the intersection of a plane perpendicular to the gel medium and the gel medium. Ideally, the thinnest gel medium is desirable, at least from the standpoint of separation of the sample consistently and also from the standpoint of ease of transfer of the sample to a permanent record, typically made of cellulose material. Such transfer is achieved by placing the finished electrophoretic separation against the medium to receive the transfer and applying an electrical field perpendicular to that applied during electrophoresis. This results in driving the sample matrix out of the gel and into the cellulose or other transfer media for permanent storage. However, because of the nature of media and gels and the electrical fields which can be created therein, such transfers are not easily or well achieved in the case of thicker gels. In addition, thinner gels have the advantage of allowing faster electrophoretic separation. Thus, the design of a most effective and easy to use electrophoretic system specifies extremely thin gels. The thinness of these gels, of course, varies for the various gel media involved and the application desired.

While the above would appear to be a straightforward approach to the design of an ideal cell, unfortunately, because of the fact that the interface between the sample solution and the gel edge must be a clean, small area equal in thickness to the thickness of the gel, a situation is created in which a thinner gel creates problems which would suggest that the gel should be as thick as possible. More particularly, during electrophoresis, it is desirable to have as large a surface area as possible for entry of the sample into the electrophoretic gel. Naturally, in order for such an area to be made, the thickness of the gel must be increased. The large area is required in order to provide for the entry of the sample into the edge of the medium in a relatively short period of time. However, increasing the thickness of the medium creates the other problems discussed above. At present, electrophoretic cell design involves an optimization of both factors, recognizing that improving the operation of the system from one standpoint results in decreasing effectiveness of other parameters of the electrophoretic system.

In an attempt to overcome this problem some cells have been manufactured in which the combs are relatively tall, resulting in the production of tall, thin reservoirs for holding sample in buffer solutions. However, the use of a tall reservoir results in large distances for a certain portion of the sample to transverse on its way from, for example, the top of the reservoir to the interface between the sample-buffer solution and the electrophoretic gel. This results in increasing the time over which a particular constituent of the sample buffer solution will be transferred into the gel media and thus the thickness of the band which is made by the system at the end of the electrophoretic separation process. Thus, the use of tall combs and tall reservoirs does not provide an acceptable solution.

SUMMARY OF THE INVENTION

The invention, as claimed, is intended to provide a remedy. It solves the problem of how to manufacture an electrophoretic cell which is of relatively great structural integrity and which achieves that structural integrity at a lower cost per unit as compared to conventional cells. At the same time the invention contemplates a novel cell structure which simplifies handling and greatly reduces the incidence of discarded cells.

In accordance with the preferred embodiments, the inventive electrophoretic cell comprises a base member defining a planar support surface. A layer of electrophoretic gel medium is disposed on the planar support surface. A top face is disposed over the layer of gel. The gel lies between the top face and the base member. Either the top face or the base member is made of transparent material. A plurality of reservoirs is defined between the top face and the base member by the top face and base member.

In accordance with the preferred embodiment, the reservoirs are defined by a plurality of walls disposed between the top face and the base member. The walls may be integral with the base member and both made of plastic. It is contemplated that the base member be an injection molded plastic element. The reservoirs are tapered in cross-section, having a smaller size adjacent an edge of the gel layer and becoming larger to form a tapered or funnel shaped reservoir at points removed from the interface of the reservoir and the gel layer. A pair of ledges is provided at opposite ends of the base member to define a space to house the gel layer. The edges of the cell have tapered facets which facilitate the application of a sealant by providing a large space to receive the same and this large space communicates with a substantially flush interface between the top face and base member. Finally, in accordance with the preferred embodiment, the edge of the electrophoretic cell adjacent the space receiving sealant is provided with a band of material which is adhered thereto, whereby additional strength is provided for the electrophoretic cell.

BRIEF DESCRIPTION OF THE DRAWINGS

One way of carrying out the invention is described in detail below with reference to drawings which illustrate only one specific embodiment of the invention and in which:

FIG. 1 is a top view of an electrophoretic cell constructed in accordance with the present invention;

FIG. 2 is a view of the output side of the electrophoretic cell along lines 2—2 of FIG. 1;

FIG. 3 is a view of the input side of the electrophoretic cell of FIG. 1 along lines 3—3 of FIG. 1;

FIG. 4 is a top view of the base member of the electrophoretic cell of FIG. 1 without the top face and gel material;

FIG. 5 is an enlarged cross-sectional view along lines 5—5 of FIG. 1;

FIG. 6 is an enlarged cross-sectional view along lines 6—6 of FIG. 1 and together with FIG. 5 illustrating the formation of input cells for multiple sample use of the inventive cell;

FIG. 7 illustrates in detail and in enlarged size the structure for maintaining the cell as a single unitary member;

BEST MODE FOR CARRYING OUT THE INVENTION

Figure 8:
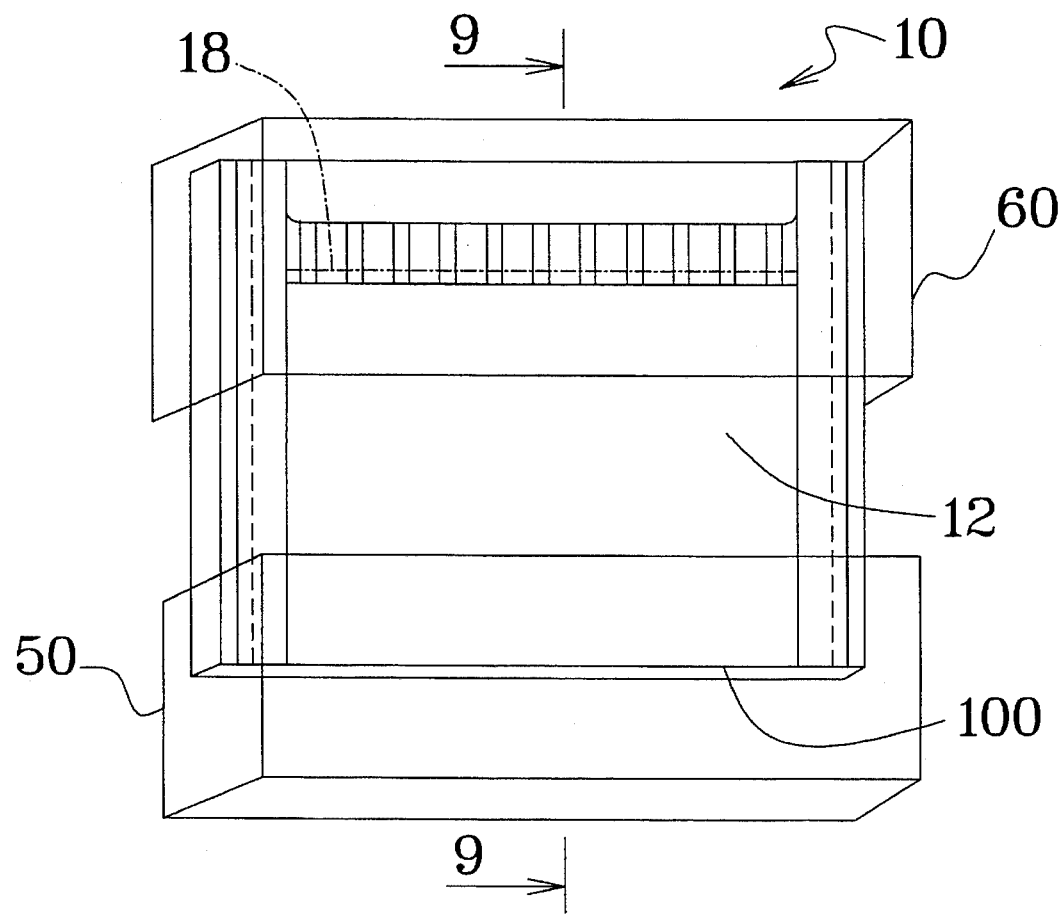
FIG. 8 is an isometric view of the cell of FIG. 1 during use.

Referring to FIGS. 1–3, an electrophoretic cell 10 constructed in accordance with the present invention is illustrated. Cell 10 generally comprises a glass top face 12 and a base member 14. In accordance with the preferred embodiment, base 14 is made of any suitable transparent plastic material, such as Lucite® plastic or the like. Base member 14 can be made by machining a plastic plate, or, in accordance with the preferred embodiment, is made by injection molding of this part.

Sandwiched between base 14 and top face 12 is a layer of electrophoretic gel 16, which extends from an input interface 18 to an output interface 20.

As discussed above, in order for an electrophoretic cell to be used in many common applications, it is necessary that means be provided for separation of a multitude of samples, typically a mixture of known and unknown solutions of materials to be electrophoretically separated. As can be seen most clearly in FIG. 4, the same is provided by forming the base 14 to have a plurality of separator walls 22.

As can be seen in FIGS. 5 and 6, walls 22 are integral with base member 14 and extend from base 14 to top base 12 and together therewith form a plurality of input reservoirs 24 (typically two to fifteen) for containing the sample to be electrophoretically separated. A small quantity of silicone sealant 25 provides the necessary water tightness between the reservoirs.

The clearance 24 necessary to provide for the layer of gel 16 is provided by a pair of outer ledges 26 and 28 at opposite ends of the cell 10. In addition, structural integrity is provided by a pair of bands 30 and 32 made of non-woven material which are secured to base 14 and top base 12. As illustrated most clearly in FIG. 7, each of the bands, such as band 32 in adhered by a layer of silicone or other adhesive 34 which also extends into the region 36 defined by the bottom 38 of glass top face 12 and the edge shaped facet 40 of base 14.

As can be seen in FIG. 4, both sides of base 14 have a wedge shaped facet 40. Finally, additional structural stability is provided by a small quantity of rubber cement 42 which is used during assembly to provide the initial setting of the base member to the face to allow for the facile and proper application of caulking 34.

Figure 9:
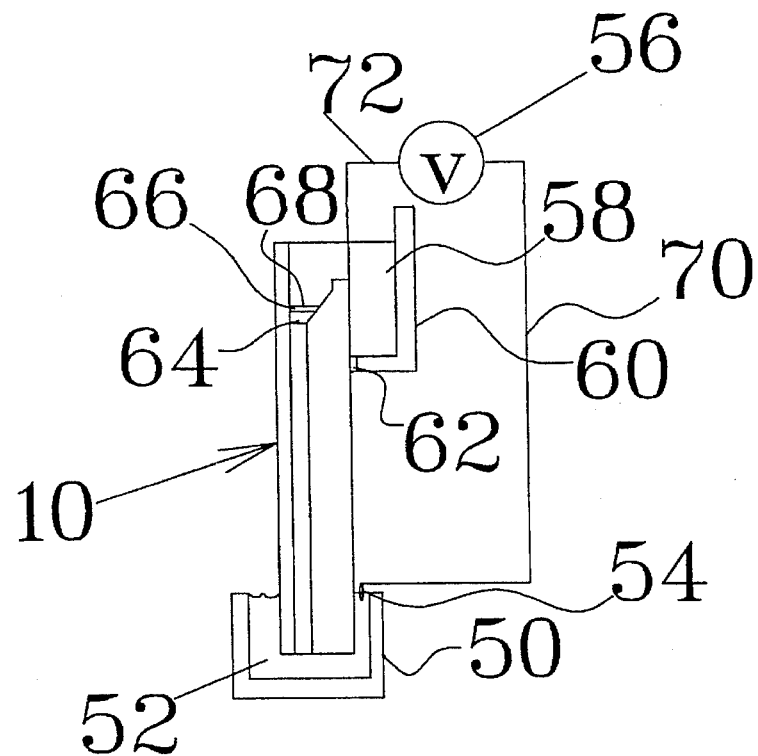
FIG. 9 is a schematic view of the electrophoretic cell of FIG. 1 during use.
Figure 10:
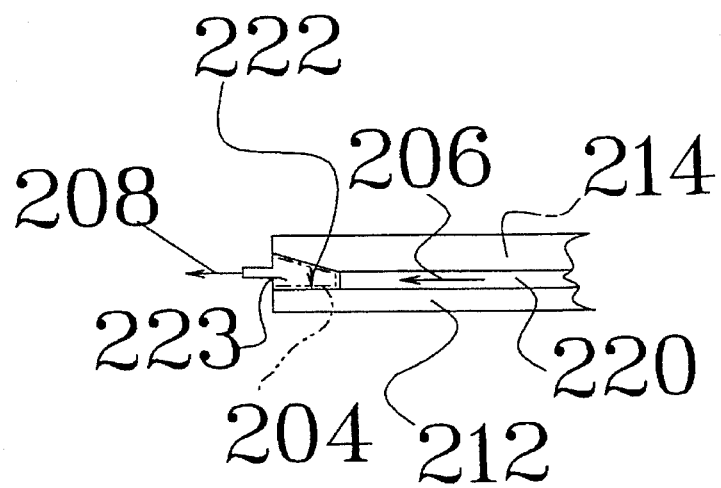
FIG. 10 is a schematic view of an alternative embodiment of the invention.

During use, as illustrated in FIGS. 8 and 9, it is necessary to apply an electric field across the electrophoretic cell and to provide for the migration of a sample. This is achieved by putting the cell 10 in a container 50 which is filled with a buffer solution 52 and provided with electricity by a standard electrode 54 which is driven by a conventional source of voltage 56.

In similar fashion the buffer solution 58, at the top of the cell, is contained by a reservoir 60 which is sealed to cell 10 by a gasket 62. This allows the buffer solution 58 to completely surround and electrically engage a sample 64 which is contained between walls 22, resulting in an interface 66 between sample 64 and buffer solution 58. Electrostatic potential is provided to buffer 58 at the other side of source 56 by an electrode 68. Electrodes 54 and 68 are coupled to source 56 by wires 70 and 72, respectively.

INDUSTRIAL APPLICABILITY

The present invention is particularly suitable for application to modern research processes. In particular, in accordance with the preferred embodiment of the invention, as alluded to above, lower costs are provided through the use of a base member with integral walls 22. In addition, the inventive electrophoretic cell is made of parts which may be easily reused, thus reducing waste and further reducing costs.

In particular, it is possible for the bands 30 and 32 to be peeled away, as illustrated in FIG. 1. Band 30 may be removed and the cell hingedly opened about band 32 in the manner that a book may be opened with band 32 functioning as the spine of the book. Because the glass top face 12 and plastic base have different properties, the gel will tend to adhere to one of them and thus maintain its integrity and not be torn of course, any two dissimilar materials will give similar results. If desired the electrophoretic layer may be further removed and adhered to a sheet of paper, or the like, thus resulting in a permanent low bulk record. The remaining base plate and top face can than be sent to the manufacturer to be reused, thus reducing substantially the waste material produced by the system, as well as lessening the likelihood that the normally toxic electrophoretic materials will be improperly discarded.

Another alternative is that the gap between the tops of wedge separator walls 22 and top base 12 be increased from a size small enough to provide capillary action after pressure filling from bottom edge 100 (FIG. 8) to a size which allows conventional pressure filling. In this case, a conventional comb is used to mold the unpolymerized gel medium and prevent it from filling the wedge-shaped reservoirs between the walls. Such thicker layers also appear to have the advantage of polymerizing more completely.

Yet another alternative is mould base member 24 without walls and place a comb 204 into the wedge shaped gap 222 between base member 214 and face 212. In the conventional manner the gel 220 is pumped in the direction of arrow 206 to form a gel wedge 223. The comb 204 is then withdrawn in the direction of arrow 208,, after polymerization occurs. The polymerized wedge 223 can not tip over like a flat divider because it is wedge-shaped and rests in a tapered gap 222.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. An electrophoretic cell, comprising:
    (a) a base member defining a planar support surface;
    (b) a layer of electrophoretic gel medium disposed on said planar support surface;
    (c) a top face disposed over said layer of gel, said layer of gel lying between said top face and said base member, one of said top face or said base member being made of transparent material, said base member and said top face being secured to each other at a pair of side ledges; and
    (d) a plurality of reservoirs positioned between said top face and said base member, and defined by said top face and said base member, a portion of at least one of said top face and said base member being tapered in cross-section so as to define said reservoirs being tapered in cross-section each of said reservoirs having a smaller size adjacent an edge of said gel layer and becoming larger to form a tapered or funnel shaped reservoir, and said reservoirs being defined by a plurality of walls integrally formed with either of said top face and said base member and disposed between said top face and said base member, said edge of said gel layer, for each of said reservoirs, being defined between a respective pair of said walls and said top face and said base member, edges of said cell adjacent said side ledges having tapered facets which facilitate the application of a sealant by providing a large space to receive the same, said large space communicating with a substantially flush interface between said top face and said base member.

2. An electrophoretic cell as in claim 1, wherein the edge of the electrophoretic cell adjacent said space receiving sealant is provided with a band of material which is adhered thereto whereby additional strength is provided for said electrophoretic cell.

3. An electrophoretic cell, comprising:

(a) a base member defining a planar support surface;

(b) a layer of electrophoretic gel medium disposed on said planar support surface;

(c) a top face disposed over said layer of gel, said layer of gel lying between said top face and said base member, one of said top face or said base member being made of transparent material; and (d) a plurality of reservoirs positioned between said top face and said base member, and defined by said top face and said base member, a portion of at least one of said top face and said base member being tapered in cross-section so as to define said reservoirs being tapered in cross-section each of said reservoirs having a smaller size adjacent an edge of said gel layer and becoming larger to form a tapered or funnel shaped reservoir, and said reservoirs being defined by a plurality of walls integrally formed with either of said top face and said base member and disposed between said top face and said base member, said edge of said gel layer, for each of said reservoirs, being defined between a respective pair of said walls and said top face and said base member, wherein a pair of ledges are provided at opposite ends of the base member to define a space to contain said gel layer, edges of said cell adjacent said ledges having tapered facets which facilitate the application of a sealant by providing a large space to receive the same, said large space communicating with a substantially flush interface between said top face and said base member.

4. An electrophoretic cell as in claim 3, wherein the edge of the electrophoretic cell adjacent said space receiving sealant is provided with a band of material which is adhered thereto whereby additional strength is provided for said electrophoretic cell.

5. An electrophoretic cell, comprising:

(a) a base member defining a planar support surface;

(b) a layer of electrophoretic gel medium disposed on said planar support surface;

(c) a top face disposed over said layer of gel, said layer of gel lying between said top face and said base member, one of said top face or said base member being made of transparent material; and (d) a plurality of reservoirs positioned between said top face and said base member, and defined by said top face and said base member, a portion of at least one of said top face and said base member being tapered in cross-section so as to define said reservoirs being tapered in cross-section each of said reservoirs having a smaller size adjacent an edge of said gel layer and becoming larger to form a tapered or funnel shaped reservoir, and said reservoirs being defined by a plurality of walls integrally formed with either of said top face and said base member and disposed between said top face and said base member, said edge of said gel layer, for each of said reservoirs, being defined between a respective pair of said walls and said top face and said base member; and (e) wherein a pair of ledges are provided at opposite ends of the said base member to define a space to contain said gel layer, edges of said cell adjacent said ledges having tapered facets which facilitate the application of a sealant by providing a large space to receive the same, said large space communicating with a substantially flush interface between said top face and said base member.

6. An electrophoretic cell as in claim 5, wherein the edge of the electrophoretic cell adjacent said space receiving sealant is provided with a band of material which is adhered thereto whereby additional strength is provided for said electrophoretic cell.

7. An electrophoretic cell as in claim 6, wherein said reservoirs are defined by a plurality of walls disposed between said top face and said base member.

8. An electrophoretic cell as in claim 7, wherein said walls are integral with said base member.

9. An electrophoretic cell as in claim 6, wherein said walls are integral with said base member, and said base member and walls are made of plastic.

10. An electrophoretic cell as in claim 9, wherein said base member is an injection molded plastic element.

11. An electrophoretic cell as in claim 10, wherein said reservoirs are tapered in cross-section, having a smaller size adjacent an edge of said gel layer and becoming larger to form a tapered or funnel shaped reservoir.

12. An electrophoretic cell, comprising:

(a) a base member defining a planar support surface;

(b) a layer of electrophoretic gel medium disposed on said planar support surface;

(c) a top face disposed over said layer of gel, said layer of gel lying between said top face and said base member, one of said top face or said base member being made of transparent material; and (d) a plurality of reservoirs positioned between said top face and said base member, and defined by said top face and said base member, a portion of at least one of said top face and said base member being tapered in cross-section so as to define said reservoirs being tapered in cross-section each of said reservoirs having a smaller size adjacent an edge of said gel layer and becoming larger to form a tapered or funnel shaped reservoir, and said reservoirs being defined by a plurality of walls integrally formed with either of said top face and said base member and disposed between said top face and said base member, said edge of said gel layer, for each of said reservoirs, being defined between a respective pair of said walls and said top face and said base member, wherein said base member and said top face have different gel adhering characteristics.

13. An electrophoretic cell, comprising:

(a) a base member defining a planar support surface;

(b) a layer of electrophoretic gel medium disposed on said planar support surface;

(c) a top face disposed over said layer of gel, said layer of gel lying between said top face and said base member, one of said top face or said base member being made of transparent material;

(d) a plurality of reservoirs positioned between said top face and said base member, and defined by said top face and said base member; and (e) a pair of ledges provided at opposite ends of the base member to define a space to contain said gel layer, edges of said cell adjacent said ledges having tapered facets which facilitate the application of a sealant by providing a larger space to receive the same, said larger space communicating with a substantially flush interface between said top face and said base member.

* * * * *